United States Patent [19]

Solodovnik et al.

[11] Patent Number: 4,771,082
[45] Date of Patent: Sep. 13, 1988

[54] POLYURETHANE FOAM COMPOSITION FOR IMMOBILIZATION IN TRAUMATOLOGY

[76] Inventors: Valentin D. Solodovnik, ulitsa Novatorov, 36, korpus 9, kv. I5; Irina L. Lir, prospekt Mira, I08, kv. 357; Anatoly B. Davydov, ulitsa Krasny Kazanets, I9, korpus I, kv. 283; Agnessa S. Scherbak, Leningradskoe shosse, 4I, korpus 2, kv. 37; Igor A. Ljukevich, Trekhgorny val, 3, kv. II; Viktor V. Cherkashin, Leninsky prospekt, 44, kv. 224, all of Moscow, U.S.S.R.

[21] Appl. No.: 130,874

[22] PCT Filed: Jan. 30, 1986

[86] PCT No.: PCT/SU86/00006
§ 371 Date: Sep. 2, 1987
§ 102(e) Date: Sep. 2, 1987

[87] PCT Pub. No.: WO87/04625
PCT Pub. Date: Aug. 13, 1987

[51] Int. Cl.⁴ ............................................. C08G 18/14

[52] U.S. Cl. ..................................... 521/110; 521/112; 521/118; 521/129; 521/131; 521/132; 521/137

[58] Field of Search ............... 521/110, 112, 118, 129, 521/131, 132, 137

[56] References Cited

U.S. PATENT DOCUMENTS

| | | | |
|---|---|---|---|
| 2,947,307 | 8/1960 | Hoppe | 128/90 |
| 3,301,252 | 1/1967 | Mahoney | 128/90 |
| 3,674,901 | 7/1972 | Shepherd et al. | 424/27 |
| 4,203,435 | 5/1980 | Krull et al. | 128/156 |

*Primary Examiner*—Maurice J. Welsh
*Attorney, Agent, or Firm*—Ladas & Parry

[57] ABSTRACT

A polyurethane foam composition for immobilization in traumatology containing the following components in mass %:
hydroxyl-containing polyester: 20–30
catalyst: 0.5–3.0
foaming agent: 0.5–7.0
foam stabilizer: 0.5–0.9
low molecular polyolefin: 20–30
polyisocyanate ensuring the ratio of the isocyanate and hydroxyl groups in the polyester equal to 1:1: the balance.

7 Claims, No Drawings

POLYURETHANE FOAM COMPOSITION FOR IMMOBILIZATION IN TRAUMATOLOGY

FIELD OF THE ART

The present invention relates to medicine and more particularly to polyurethane foam composition for immobilization traumatology.

PRIOR ART

Known is the art is a composition for preparing an immobilizing foam material based on polyurethane (U.S. Pat. No. 4,947,307, 1960, cl. 128-90), said composition containing polyester with hydroxyl groups, hexamethylenediisocyanate, tertiary amine a catalyst, and water as a foaming agent. Such a composition is characterized by a high viscosity of polyester which hinders or makes impossible its use in nonstationary conditions and by considerable heat liberation caused by a high activity of primary hydroxyl groups in polyesters. Considerable heat liberation necessitates (to avoid burns) the use of polyesters with a low content of hydroxyl groups and this fact, in its turn, decreases the rigidity of polyurethane foam.

Also known in the art is a composition (U.S. Pat. No. 3,301,252, 1967, cl. 128-90) for preparing a rigid immobilizing foam material containing aromatic polyether which is a product of condensation of 1.1.3-hydroxyphenylpropane and propylene oxide with a hydroxyl number of about 380, polyphenylmethanepolyisocyanate containing from 40 to 60 mass % of 4,4-diphenylmethanediisocyanate, trichlorofluoromethane as a foaming agent, 1-methyl-4-dimethylaminoethylpiperazine as a catalyst, and block copolymer of siloxane and oxyalkylene as a foam stabilizer.

The disadvantages of this composition reside in a high viscosity of aromatic polyether, high temperature of the formation of polyurethane foam, and toxicity of the catalyst.

Likewise known in the art is a composition (The Author's Certificate of the USSR No. 433181, 1971, cl. C 08 G 18/14) containing as a hydroxil-containing compound a mixture of N,N,N',N'-tetraoxypropylethylenediamine and polyether based xylite in a ratio of 1:9-4:6, respectively, polyisocyanate, and a foaming agent.

The above composition is also disadvantageous in that the temperature of formation of polyurethane foam is high.

Also known in the art is a composition (The Author's Certificate of the USSR No. 990213, 1975, cl. A 61 F 1/00) containing the following components (mass %):
foaming agent: 1-40
hydroxyl-containing polyester: 25-45
polyhydroxyl-containing tertiary amine: 1.6-14
monohydroxyl-containing tertiary amine: 0.16-2.3
hydroxyl-free tertiary amine: 0.16-3.2
polyisocyanate in amount ensuring the ratio of isocyanate and hyroxyl groups in polyester equal to 1:1: the balance.

As a hydroxyl-containing polyester use is made of the products of oxyalkylation of polyatomic alcohols and as a foam stabilizer-of an organosilicon compound. The composition ensures a required rate of the formation of polyurethane foam and of hardening at lowered temperature but high heat liberation calls for the use of heat insulating fillers to avoid burning the skin of the patient.

DISCLOSURE OF THE INVENTION

The main object of the invention is to prepare a polyurethane foam composition by introducing a new component and changing a qualitative ratio of the initial components, said composition having a low foaming temperature and improved water resistance which rules out a possible burning the skin of the patient.

Said object is accomplished by that the propoposed polyurethane foam composition for immobilization in traumatology containing hydroxyl-containing polyester, a catalyst, a foaming agent, a foam srabilizer, and polyisocyanate in the amount ensuring the ratio of the isocyanate and hydroxyl groups of the polyester equal to 1:1, according to the invention, contains additionally a low-molecular polyolefin at a following ratio of the initial component (mass %):
hydroxyl-containing polyester: 20-30
catalyst: 0.5-3.0
foaming agent: 0.5-7.0
foam stabilizer: 0.5-0.9
low-molecular polyolefin: 20-33
polyisocyanate ensuring the ratio of isocyanate and hydroxyl groups of the polyester equal to 1:1: the balance.

The introduction of a low-molecular polyolefin in amount 20-30 mass % into the composition decreases heat liberation upon hardening the foam material.

As a low molecular polyolefin said composition contains preferably vaseline oil or solid paraffin, as a hydroxyl-containing polyester—the product of oxyalkylation of polyatomic alcohol with alkylene oxide.

The proposed composition contains preferably hydroxyl-containing tertiary amine as a catalyst, trichlorofluoromethane as a foaming agent, organosilicon oligomers or the products of their oxyalkylation as a foam stabilizer, and 4,4-diphenylmethanediisocyanate or its mixture with aromatic isocyanates as polyisocyanate. This ensures the preparation from said composition of a light, X-ray transparent, nontoxic, and strong, aterial.

The proposed composition has a lower foaming temperature and improved water resistance as compared to known compositions.

THE BEST VERSION OF ACCOMPLISHING THE INVENTION

The proposed polyurethane composition for immobilization in traumotology has the following composition in mass %:
hydroxyl-containing polyester: 20-30
catalyst: 0.5-3.0
foaming agent: 0.50-7.0
foam stabilizer: 0.5-0.9
low-molecular polyolefin: 20-33
polyisocyanate ensuring the ratio of isocyanate and hydroxyl groups of the polyester equal to 1:1: the balance.

As low-molecular polyolefins use can be made of liquid and solid polyolefins, for instance, mineral oil, preferably, vaseline oil, silicone liquids and solid paraffins of mineral and synthetic origin with a molecular mass of 300-2000, preferably, solid paraffins with a melting point of 30°-80° C., for instance, polyethylene wax or paraffin, as well as other high-boiling organic liquids or solids with a similar melting point inert towards isocyanates and alcohols.

The properites of the material are determined by the amount of the introduced low-molecular polyolefin which is a heat-with-drawing component, the content thereof being 20-30 mass %. The introduction of the above component in amount less than 20 mass % increases the foaming temperature up to the values exceeding 45° C. which makes it possible to burn the skin of the patient. The amount of the heat-withdrawing component more than 30 mass % does not lead to a considerable decrease in temperature upon hardening and causes the isolation of the parrafin as an independent phase.

As hydroxyl-containing polyesters use can be made of aliphatic, alicyclic, or aromatic polyesters with a functionality or from 3 to 8 containing from 8 to 22 weight % of hydroxyl groups and also containing amino-groups, for instance, the product of oxypropylation of polyatomic alcohol (glycerin, xylite, or saccharose) nitrogen-containing polyester, N,N,N',N'-tetraoxypropylethylenediamine or a mixture thereof in a ratio of 5-30:95-70, respectively.

As a hydroxyl-containing polyester use can be made of polyesters which are, for instance, the product of condenstion of aliphatic dicarboxylic acids (adipic, phthalic) and polyatomic alcohols (butyleneglycol, hexanetriol) taken in excess with respect to the acids.

As polyisocyanate use can be made of aliphatic and aromatic polyisocyanate with a functionality of 2 and more as well as the product of interaction thereof with polyesters, preferably, 4,4-diphenylmethanediisocyanate or a its mixture with aromatic isocyanates of a higher functionality.

As catalysts use can be made of tertiary amines, organotin compounds and other compounds which promote the formation of urethanes from isocyanates, for instance, N,N-dimethylethanolamine, N,N-diethylethanolamine, triethylamine, dimethylcyclohexylamine, or a mixture thereof, preferably, N,N-dimethylethanolamine.

The presence of hydroxyl groups in a molecule of tertiary amines ensures a chemical bonding thereof with polyisocyanate and thereby a decrease in toxicity of the foam material.

As a foaming agent use can be made of low-molecular fluorinated hydrocarbons, carbon chlorides, preferably, trichlorofluoromethane and the mixtures thereof, other low-boiling inert organic liquids and water.

As a foam stabilizer use can be made of organosilicon oligomers and the products of oxyalkylation thereof.

Foaming, molding, and hardening of the composition is performed at room temperature by the following procedure: the calculated amounts of all the components except polyisocyanate are placed into a reservoir and mixed after which polyisocyanate is added to the mixture and the mixture is stirred for 30 s and then left for free foaming to take place till the time of ungluing is attained, Then the foamed mass is applied to the patient's body part being immobilized, smoothed out to a uniform layer, and kept for hardening.

The hardened foam material retains the acquired shape for a long period of time without being damaged, it does not wound the skin of the patient and is easily cut with a knife or gypsum scissors.

The proposed composition was tested in a clinic for 23 patients. In 7 cases the fixing devices were prepared by the pouring technique and in 16 cases they were made of the foam material with the use of contour polyethylene covers representing double-walled covers having the shape of the limb.

The following types of fixing devices wer prepared: longuettes for upper limbs—7, longuettes for fixing skin and foot—11, splints for fixing knee joint—3, corset for fixing the lumbar section of spine—1, cravat of the Schanz type for fixing the cervical section of spine—1.

As follows from the data of clinic observations, the application of the proposed foam material does not cause hyperemy or irritation and the foam material becomes hardened in 8-10 minutes after mixing of the components. In the process of foaming the material easily acquires the shape of the limb or any part of the body. The hardened foam material of the proposed composition possesses a high strength, water-resistance, X-ray transparency, and lightness. The immobilizing properites of the material are retained for a long period of time, and nevertheless, the material is easily cut with a knife.

The fixing elements from the foam material of the proposed composition can be used for transport and medical immobilization in the same cases when gypsum immobilization is usually used.

Thus, the proposed composition, as compared with known compositions, has essential advantages: lightness, X-ray transparency, water-resistance, low hardening temperature which rules out a possible burning of the skin.

For a better understanding of the present invention specific examples of the composition being proposed are given hereinbelow by way of illustration.

EXAMPLE 1

Polyurethane foam composition for immobilization in traumatology of the following composition (in mass %):
the product of oxypropylation of xylitol with a molecular mass of 800: 16.6
the product of oxyethylation of glycerin with a molecular mass of 350: 3.4
N,N-dimethylethanolamine: 0.5
trichlorofluoromethane: 0.5
the product of oxyethylation of dihydroxypolydimethylsiloxane with a molecular mass of 400: 0.5
paraffin with a melting point of 39°-40° C.: 33.0
a mixture (1:5) of 4,4-diphenylmethanediisocyanate and polyisocyanates of the general formula $$OCNC_6H_4CH_2[C_6H_3(NCO)\ CH_2]_nC_6H_4NCO,$$

where n=1 or 2: 45.5.

All the components in above amounts except a mixture of polyisocyanates are placed into a polyethylene cup 200 ml in volume. The components are mixed and a mixture of polyisocyanates is added. The mixture obtained is stirred for 30 s and then left for free foaming till the time of ungluing is attained. The foamed mass is molded and hardened.

Maximum temperature at the moment of foaming does not exceed 45° C. and then decreases to the ambient temperature. An apparent density of the foam material is 40 kg/m³. Neither irritation, nor hyperemy, no burning the skin of the patient was observed during clinic tests when the foam material was applied to the limb of the patient.

EXAMPLE 2

Polyurethane foam composition for immobilization in traumatology of the following composition (in mass %):

the product of oxypropylation of glycerin with a molecular mass of 400: 10.0
the product of oxyethylation of xylitol with a molecular mass of 800: 20.0
N,N-diethylethanolamine: 3.0
trichlorofluoromethane: 7.0
the product of oxyethylation of dihydroxypolydimethylsiloxane with a molecular mass of 400: 0.9
vaseline oil with a molecular mass of 350: 20.0
a mixture (1:1) of 4,4-diphenylmetanediisocyanate and polyisocyanates of the general formula $$OCNC_6H_4CH_2[C_6H_3(NCO)CH_2]_nC_6H_4NCO,$$

where n=1 or 2: 39.1.

The composition is foamed, molded, and hardened by following the procedure described in Example 1. The foaming temperature is 44°-45° C., the apparent density 41 kg/m³. No adverse effect of the foam material on the skin of the patient was observed in the course of clinic experiments.

EXAMPLE 3

Polyurethane foam composition for immobilization in traumatology of the following composition (in mass %):
the product of oxypropylation of xylitol with a molecular mass of 800: 20.75
the product of oxyethylation of glycerin with a molecular mass of 350: 4.25
N,N-dimethylethanolamine: 1.50
trichlorofluoromethane: 5.5
the product of oxyethylation of dihydroxypolydimethylsiloxane with a molecular mass of 400: 0.7
paraffin with a melting point of 35°-40° C.: 30.3
a mixture of polyisocyanates (identical to that described in Example 2): 37.0.

The composition is foamed, molded, and hardened by following the procedure described in Example 1. Maximum foaming temperature is 44°-45° C., the apparent density 40 kg/m³. No adverse effect of the foam material on the skin of the patient was observed in the course of clinic experiments.

EXAMPLE 4

Polyurethane foam composition for immobilization in traumatology of the following composition (in mass %):
the product of oxypropylation of xylitol with a molecular mass of 800: 20.75
the product of oxyethylation of glycerin with a molecular mass of 350: 4.25
N,N-dimethylethanolamine: 1.5
trichlorofluromethane: 5.5
the product of oxyethylation of dihydroxypolydimethylsiloxane with a molecular mass of 400: 0.7
paraffin with a melting point of 35°-40° C.: 30.3
4,4-diphenylmethanediisocyanate: 37.0

The composition is foamed, molded, and hardened by following the procedure described in Example 1.

Maximum foaming temperature is 44°-45° C., the apparent density 40 kg/m³. No adverse effect of the foam material on the skin of the patient was observed in the course of clinic experiments.

EXAMPLE 5 (control)

Polyurethane foam composition for immobilization in traumatology of the following composition (in mass %):
the product of oxypropylation of xylitol with a molecular mass of 800: 29.76
the product of oxyethylation of glycerin with a molecular mass of 350: 6.09
N,N-dimethylethanolamine: 2.15
trichlorofluoromethane: 7.88
the product of oxyethylation of dihydroxypolydimethylsiloxane with a molecular mass of 400: 1.04
a mixture (1:1) of 4,4-diphenylmethanediisocyanate and polyisocyanates of the general formula $$OCNC_6H_4CH_2\,C_6H_3(NCO)CH_2\,_nC_6H_4NCO,$$

where n=1 or 2: 53.08.

The composition is foamed, molded, and hardened by following the procedure described in Example 1.

Maximum foaming temperature is 109° C., the apparent density 17 kg/m³. The application of the foam material to the hair-free skin of the rats causes burning of II-III degrees.

INDUSTRIAL APPLICABILITY

The proposed polyurethane foam composition can be used as an immobilizing material for medical aid in the case of breaks, wounding, and other trauma of the extremities both under hospital and home conditions.

We claim:

1. A polyurethane foam composition for immobilization in traumatology containing a hydroxyl-containing polyester, catalyst, foaming agent, foam stabilizer, polyisocyanate in amount ensuring the ratio of isocyanate and hydroxyl groups in polyester equal to 1:1, characterized in that the composition contains additionally a low-molecular polyolefin, the above components being in the following ratio, mass %:
hydroxyl-containing polyester: 20-30
catalyst: 0.5-3.0
foaming agent: 0.5-7.0
foam stabilizer: 0.5-0.9
low molecular polyolefin: 20-33
polyisocyanate ensuring the ratio of isocyanate and hydroxyl groups in polyester equal to 1:1: the balance.

2. A polyurethane foam composition as claimed in claim 1, characterized in that as a low molecular polyolefin it contains vaseline oil or solid paraffin.

3. A polyurethane foam composition as claimed in claim 1, characterized in that as a hydroxyl-containing polyester it contains the product of oxyalkylation of polyatomic alcohol with alkylene oxide.

4. A polyurethane foam composition as claimed in claim 1, characterized in that as a catalyst it contains hydroxyl-containing tertiary amine.

5. A polyurethane foam composition as claimed in claim 1, characterized in that as a foaming agent it contains trichlorofluoromethane.

6. A polyurethane foam composition as claimed in claim 1, characterized in that as foam stabilizer it contains organosilicon oligomers or the product of oxyalkylation thereof.

7. A polyurethane composition as claimed in claim 1, characterized in that as polyisocyanate it contains 4,4-diphenylmethanediisocyanate or a mixture thereof with aromatic isocyanates.

* * * * *